United States Patent [19]

Schaub et al.

[11] 4,404,195
[45] Sep. 13, 1983

[54] POLY CATION SALTS OF MONOHEXOSETHIO (OR OXY) ALKYL DIAMIDES

[75] Inventors: Robert E. Schaub, Upper Saddle River, N.J.; Janis Upeslacis, Pomona; Seymour Bernstein, New City, both of N.Y.

[73] Assignee: American Cyanamid Company, Stamford, Conn.

[21] Appl. No.: 369,049

[22] Filed: Apr. 16, 1982

[51] Int. Cl.$^3$ .................. A61K 31/70; C07H 15/26
[52] U.S. Cl. .................. 424/180; 536/4.1; 536/17.6; 536/118
[58] Field of Search .......... 424/180; 536/4.1, 118, 536/17.6

[56] References Cited

U.S. PATENT DOCUMENTS

| | | | |
|---|---|---|---|
| 4,258,034 | 3/1981 | Joseph et al. | 424/180 |
| 4,304,904 | 12/1981 | Nair et al. | 536/4 |
| 4,334,058 | 1/1982 | Nair et al. | 536/8 |
| 4,337,249 | 1/1982 | Conrow et al. | 424/180 |

*Primary Examiner*—Johnnie R. Brown
*Assistant Examiner*—Ciro Faraci
*Attorney, Agent, or Firm*—Anne M. Rosenblum

[57] ABSTRACT

N,N'-Bis[4-[(2,3,4,6-tetra-O-sulfo-α(or β)-D-glucopyranosyl)thio(or oxy)]phenyl]alkyl diamides, the cation salts thereof, useful as modulators of the complement system, the intermediates thereof and the process for the preparation of such intermediates and end products.

29 Claims, No Drawings

POLY CATION SALTS OF MONOHEXOSETHIO (OR OXY) ALKYL DIAMIDES

BACKGROUND OF THE INVENTION

1. Field of the Invention

The present invention relates to novel cation salts of monohexosethio (or oxy) alkyl diamides, to their use as modulators of the complement system of warm-blooded animals, to the intermediates thereof and to the process for the preparation of such intermediates and end products.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of sub-units designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W. H. O. 39: 935 (1968); Annu. Rev. Med. 19: 1 (1968); John Hopkins Med. J. 128: 57 (1971); Harvey Lect. 66: 75 (1972); N. Engl. J. Med. 287: 452, 489, 545, 592, 642 (1972); Sci. Am. 229 (5): 54 (1973); Fed. Pro. 32: 134 (1973); Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N. J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, New York and London (1977); Am. J. Clin. Pathol. 68: 647 (1977); Biochem. Soc. Trans. 5: 1659 (1977); Harvey Lect. 72: 139 (1976–1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes can become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestions regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 115: 813 (1978); J. Biol. Chem. 254: 9908 (1979).

A variety of substances have been disclosed as inhibiting the complement system, i.e., as complement inhibitors. For example, the compounds, 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anticomplementary effect, Br. J. Exp. Pathol. 33: 327 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim. Biophys. Acta 317: 539 (1973); Life Sci. 13: 351 (1973); J. Immunol. 113: 584 (1974); Immunology 26: 819 (1974); J. Med. Chem. 17: 1160 (1974); Biochim. Biophys. Res. Comm. 67: 225 (1975); Ann. N. Y. Acad. Sci. 256: 441 (1975); J. Med. Chem. 19: 634, 1079 (1976); J. immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

The instant invention relates to new compounds, the poly cation salts of monohexosethio (or oxy) alkyl diamides, that modulate the complement system, thereby modulating complement activity in body fluids. Moreover, this invention involves a method of modulating the complement system in a body fluid which comprises subjecting body fluid complement to the action of an effective complement modulating amount of the above-identified compounds. This invention further concerns a method of modulating the complement system in a warm-blooded animal which comprises administering to said animal an effective complement modulating amount of the above-identified compounds.

This invention also deals with the novel precursors that act as intermediates in preparing the above-described complement modulating compounds of this invention.

DETAILED DESCRIPTION OF THE INVENTION

In accordance with the present invention, there are provided novel compounds represented by the following generic Formula I:

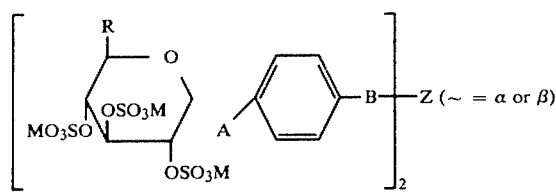

wherein M is a nontoxic pharmaceutically acceptable cation salt, wherein the salt forming moiety is selected from the group consisting of alkali metal, alkaline earth metal, aluminum, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$); A is selected from the group consisting of —S— and —O—; B is selected from the group consisting of —NHCO—, —NHSO$_2$— and —NHCH$_2$—; R is selected from the group consisting of CH$_2$OSO$_3$M, COOCH$_3$ and COOM; and Z is a straight or branched chain alkylidene group —(CH$_2$)$_m$—, where m is an integer 0–12, inclusive, with the proviso that when m is zero or one, B cannot be —NHSO$_2$—, which compounds are highly active as complement modulators.

Although the compounds of Formula I are shown as being fully sulfated, this invention contemplates partially sulfated products.

In addition, this invention is concerned with the precursors in the preparation of the complement modulating compounds of Formula I, shown by the following Formula II:

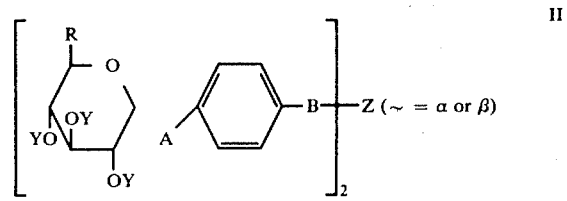

wherein A, B and Z are as described in Formula I; Y is selected from the group consisting of —H and —COCH$_3$; and R is selected from the group consisting of —CH$_2$OY; —COOH and —COOCH$_3$.

Particularly preferred compounds of Formula I which are of major interest as modulators of the complement system include the following:

octasodium N,N'-bis[4-[(2,3,4,6-tetra-O-sulfo-β-D-glucopyranosyl)thio]phenyl]pentanediamide
hexasodium(1,4-dioxo-1,4-butanediyl)bis(imino-4,1-phenylene)bis(2,3,4-tri-O-sulfo-1-thio-β-D-glucopyranosiduronic acid), dimethyl ester
octasodium(1,5-dioxo-1,5-pentanediyl)bis(imino-4,1-phenylene)bis(2,3,4-tri-O-sulfo-1-thio-β-D-glucopyranosiduronic acid
octatriethylammonium N,N'-bis[4-[(2,3,4,6-tetra-O-sulfo-β-D-glucopyranosyl)thio]phenyl]pentanediamide
hexatriethylammonium(1,4-dioxo-1,4-butanediyl)bis-(imino-4,1-phenylene)bis(2,3,4-tri-O-sulfo-1-thio-β-D-glucopyranosiduronic acid), dimethyl ester
octatriethylammonium(1,5-dioxo-1,5-pentanediyl)bis-(imino-4,1-phenylene)bis(2,3,4-tri-O-sulfo-1-thio-β-D-glucopyranosiduronic acid)

Specific compounds of Formula II which are of particular interest as precursors in the production of the compounds of Formula I include the following:

N,N'-bis[4-[(2,3,4,6-tetra-O-acetyl-β-D-glucopyranosyl)thio]phenyl]pentanediamide
N,N'-bis[4-[(β-D-glucopyranosyl)thio]phenyl]pentanediamide
(1,4-dioxo-1,4-butanediyl)bis(imino-4,1-phenylene)-bis(2,3,4-tri-O-acetyl-1-thio-β-D-glucopyranosiduronic acid), dimethyl ester (1,4-dioxo-1,4-butanediyl)bis(imino-4,1-phenylene)-bis(1-thio-β-D-glucopyranosiduronic acid), dimethyl ester (1,5-dioxo-1,5-pentanediyl)bis(imino-4,1-phenylene)-bis(2,3,4-tri-O-acetyl-1-thio-β-D-glucopyranosiduronic acid), dimethyl ester (1,5-dioxo-1,5-pentanediyl)bis(imino-4,1-phenylene)-bis(1-thio-β-D-glucopyranosiduronic acid)

Other representative compounds of this invention are the following:

octasodium N,N'-bis[4-[(2,3,4,6-tetra-O-sulfo-β-D-glucopyranosyl)oxy]phenyl]pentanediamide hexasodium(1,4-dioxo-1,4-butanediyl)bis(imino-4,1-phenylene)bis(2,3,4-tri-O-sulfo-1-oxy-β-D-glucopyranosiduronic acid), dimethyl ester octasodium(1,5-dioxo-1,5-pentanediyl)bis(imino-4,1-phenylene)bis(2,3,4-tri-O-sulfo-1-oxy-β-D-glucopyranosiduronic acid octatriethylammonium N,N'-bis[4-[(2,3,4,6-tetra-O-sulfo-β-D-glucopyranosyl)oxy]phenyl]pentanediamide hexatriethylammonium(1,4-dioxo-1,4-butanediyl)bis-(imino-4,1-phenylene)bis(2,3,4-tri-O-sulfo-1-oxy-β-D-glucopyranosiduronic acid), dimethyl ester octatriethylammonium(1,5-dioxo-1,5-pentanediyl)bis-(imino-4,1-phenylene)bis(2,3,4-tri-O-sulfo-1-oxy-β-D-glucopyranosiduronic acid)

This invention further deals with a method of modulating the complement system in a body fluid, such as blood serum, which comprises subjecting body fluid complement to the action of an effective complement modulating amount of a compound of the above Formula I. Body fluids can include blood, plasma, serum, synovial fluid, cerebrospinal fluid, or pathological accumulations of fluid such as pleural effusion, etc. This invention also concerns a method of modulating the complement system in a warm-blooded animal which comprises administering to said warm-blooded animal an effective complement modulating amount of a compound of Formula I.

The compounds of Formula I find utility as complement modulators in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having nonimmunologic diseases such as paroxysmal nocturnal hemoglobinurea, hereditary angioneurotic edema and inflammatory states induced by the action of bacterial or lysosomal enzymes on the appropriate complement components as, for example, inflammation following coronary occlusion. They also may be useful in the treatment of transplant rejection and ulcers and as blood culture and transport mediums. The sulfated compounds of this invention such as the sodium and aluminum salts, may be particularly useful in the treatment of ulcers and the like on oral therapy. Also, the non-sulfated intermediate compounds of formula II may be useful as immuno-enhancing agents or potentiators.

The compounds of this invention may be prepared according to the following flowchart.

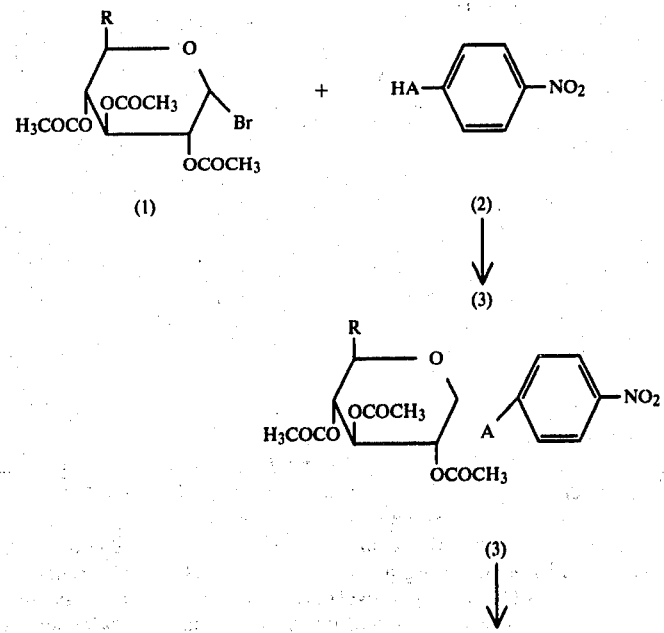

FLOWCHART

FLOWCHART

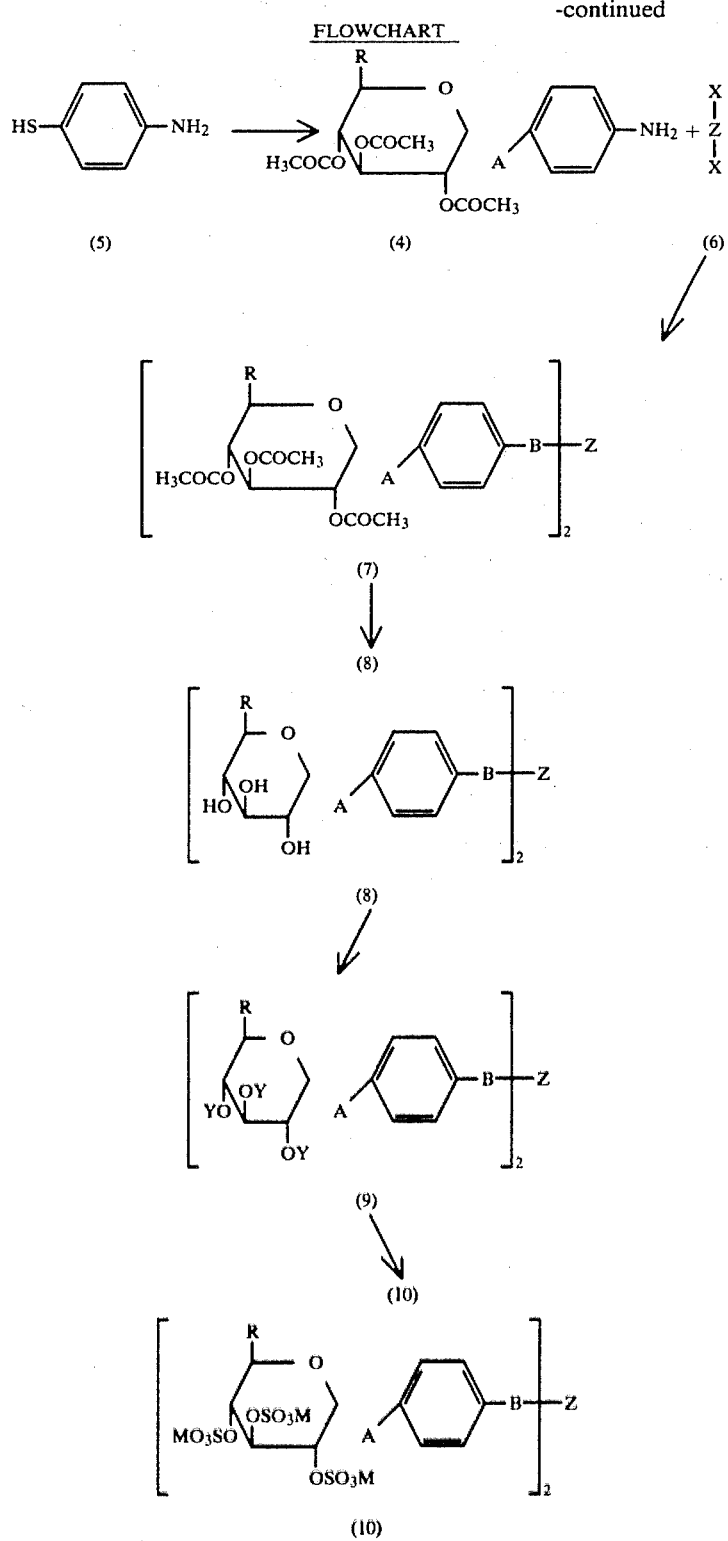

In accordance with the above flowchart, a bromoacetyl pyranoside (1) [where R is $CH_2OCOCH_3$ or $COOCH_3$] is reacted with a p-nitrothio(or oxy)phenyl (2) [where A is —S— or —O—] and sodium hydride in a solvent such as dimethoxyethane, under an inert atmosphere for several hours, giving a 4-nitrophenyl 2,3,4-tri-O-acetyl-α(or β)-D-glucopyranosyl)-1-thio(or oxy) derivative (3) which is then catalytically reduced to the corresponding 4-aminophenyl derivative (4). Alternatively, similar reaction of (1) with p-aminothiophenol (5) produces (4) directly without requiring reduction. The derivative (4) is then treated with an acid chloride (6) [where X is —COCl or —$SO_2Cl$; Z is $(CH_2)_m$; and m is an integer 0–12] in a solvent such as acetonitrile under an inert atmosphere for several hours, giving a N,N'-bis[4-[(2,3,4-tri-O-acetyl-α(or β)-D-glucopyranosyl)thio(or oxy)]phenyl]alkyldiamide or alkylsulfonamide (7) [where Z is as described above and B is —NHCO— or —NHSO$_2$—]. The derivative (7) is then reacted with ammonia-saturated methanol at −5° to +5° C. under an inert atmosphere or with sodium in methanol for several hours, giving N,N'-bis[4-[(α(or β)-D-glucopyranosyl)thio(or oxy)]phenyl]alkyldiamide or alkylsulfonamide (8). Derivative (8) is then reacted with triethylamine-sulfur trioxide complex in N,N-dimethylacetamide, under an inert atmosphere at 60°–65° C. for several hours, giving the polytriethylammonium derivative (9) [where Y is SO$_3^-$.NH$^+$-(C$_2$H$_5$)$_3$], which is then, if desired, reacted with a cation-containing compound wherein the salt forming moiety is selected from the group consisting of alkali metal, alkaline earth metal, aluminum, ammonia and substituted ammonia selected from the group consisting of piperidine, pyrazine, alkanolamine (C$_2$–C$_6$) and cycloalkylamine (C$_3$–C$_6$), and thereafter precipitated in ethanol, giving the end product (10) [where M is as described in the above Formula I].

It is generally preferred that the respective product of each process step, described hereinabove, is separated and/or isolated prior to its use as starting material for subsequent steps. Separation and isolation can be effected by any suitable purification procedure such as, evaporation, crystallization, column chromatography, thin-layer chromatography, distillation, etc. Also it should be appreciated that when typical reaction conditions (e.g., temperatures, mole ratios, reaction times) have been given, the conditions which are both above and below these specified ranges can also be used, though generally less conveniently.

The term "pharmaceutically acceptable salts" refers to those salts of the parent compound which do not significantly or adversely affect the pharmaceutical properties (e.g., toxicity, effectiveness, etc.) of the parent compound. The salt forming moieties of the present invention which are pharmaceutically acceptable include the alkali metals (e.g., sodium, potassium, etc.); alkaline earth metals (e.g., calcium, etc.); aluminum; ammonia; and substituted ammonia selected from the group consisting of trialkylamine (C$_1$–C$_6$), piperidine, pyrazine, alkanolamine (C$_2$–C$_6$) and cycloalkylamine (C$_3$–C$_6$).

The term "trialkylamine (C$_1$–C$_6$)" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "alkanolamine (C$_2$–C$_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine (C$_3$–C$_6$)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 25° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

Whereas the exact scope of the instant invention is set forth in the appended claims, the following specific examples illustrate certain aspects of the present invention. However, the examples are set forth for illustration only and are not to be construed as limitations on the present invention except as set forth in the appended claims.

A further understanding of the invention can be obtained from the following non-limiting Preparations and Examples.

EXAMPLE 1

N,N'-Bis[4-[(2,3,4,6-tetra-O-acetyl-β-D-glucopyranosyl)thio]phenyl]pentanediamide To a mixture of 3.0 g of 50% sodium hydride in oil dispersion in 40 ml of dry dimethoxyethane under argon was added dropwise a solution of 8.7 g of 4-aminothiophenol in 70 ml of dry dimethoxyethane. The mixture was stirred for 3.5 hours, then a solution of 25.5 g of α-D-bromoglucose tetraacetate in 70 ml of dry dimethoxyethane was added dropwise at a fast rate. The mixture was stirred overnight, filtered through diatomaceous earth and the filtrate evaporated to a glass. This glass was dissolved in 150 ml of dichloromethane, filtered through hydrous magnesium silicate, washed with one liter of dichloromethane, treated with charcoal and filtered through diatomaceous earth. The filtrate was evaporated to a glass which was dissolved in 150 ml of hot ether and then refrigerated overnight, giving 15.8 g of 4-aminophenylthio 2,3,4,6-tetra-O-acetyl-β-D-glucopyranoside.

To a solution of 5.0 g of the above compound in 50 ml of dry pyridine:acetonitrile (1:1) stirring under argon, was added dropwise a solution of 930 mg of glutaryl chloride in 3 ml of acetonitrile. This mixture was stirred for 2 hours, a small portion of glutaryl chloride was added, the mixture was allowed to stand overnight, then poured into 250 ml of water and stirred for 15 minutes. The resulting gum was extracted twice with chloroform, the extracts were combined, washed with 0.5% hydrochloric acid, dried, treated with charcoal and filtered through diatomaceous earth. The filtrate was evaporated to a glass which was dissolved in 100 ml of chloroform, filtered through hydrous magnesium silicate, washed with 600 ml of chloroform and evaporated, giving the desired intermediate as 4 g of a tan glass.

EXAMPLE 2

N,N'-Bis[4-[(β-D-glucopyranosyl)thio]phenyl]pentanediamide

To 4.0 g of N,N'-bis[4-[(2,3,4,6-tetra-O-acetyl-β-D-glucopyranosyl)thio]phenyl]pentanediamide was added 500 ml of ammonia saturated methanol at 0° C. The solution was kept at 0° C. for 2 hours, then at ambient temperature overnight and taken to dryness in vacuo. The residue was triturated with 20 ml of absolute ethanol and the resulting solid was collected, giving 1.45 g of the desired intermediate as an amorphous solid.

EXAMPLE 3

Octasodium N,N'-bis[4-[(2,3,4,6-tetra-O-sulfo-β-D-glucopyranosyl)thio]phenyl]pentanediamide A 6.75 g portion of triethylamine-sulfur trioxide complex was dissolved in 30 ml of dry N,N-dimethylacetamide. A 6.75 g portion of 4 A molecular sieves was added and the mixture was heated at 60° C. for 15 minutes. A 1.25 g portion of N,N'-bis[4-[(β-D-glucopyranosyl)thio]phenyl]pentanediamide was added and the mixture was heated at 60° C. under argon for 4 hours, then cooled overnight, poured into 650 ml of acetone and refrigerated overnight. The resulting gum (octatriethylammonium N,N'-bis[4-[(2,3,4,6-tetra-O-sulfo-β-D-glucopyranosyl)thio]phenyl]pentanediamide) was separated, washed with acetone and added to 10 ml of water containing 1.5 g of sodium acetate. The mixture was filtered through diatomaceous earth and the filtrate added to 600 ml of absolute ethanol, stirred for 30 minutes and allowed to stand overnight. The solid was collected, washed with absolute ethanol, then ether and dried in vacuo, giving 1.57 g of the desired product.

EXAMPLE 4

(1,4-Dioxo-1,4-butanediyl)bis(imino-4,1-phenylene)-bis(2,3,4-tri-O-acetyl-1-thio-β-D-glucopyranosiduronic acid), dimethyl ester To a mixture of 700 mg of 50% sodium hydride oil dispersion in 50 ml of dry dimethoxyethane, stirred under argon was added dropwise a solution of 3.0 g of sodium 4-aminothiophenol in 25 ml of dry dimethoxyethane. The mixture was stirred for 2 hours, then a solution of 4.8 g of methyl acetobromoglucuronate in 25 ml of dry dimethoxyethane was added. The mixture was stirred overnight, filtered through diatomaceous earth, washed with dimethoxyethane and taken to dryness. The residue was taken up in chloroform, filtered through hydrous magnesium silicate, washed with one liter of chloroform and taken to dryness, giving a syrup. This syrup was chromatographed on 600 g of silica gel in a nylon column, the column being divided into 36 equal segments. Segments 15–23 were combined, suspended in ethyl acetate, filtered free of silica gel, and taken to dryness in vacuo, giving a yellow glass which was crystallized from ether, giving 4-aminophenylthio 2,3,4-tri-O-acetyl-β-D-glucopyranosiduronic acid, methyl ester as off-white crystals.

To a stirred solution of 2.0 g of the above compound in 20 ml of pyridine:acetonitrile (1:1) under argon was added dropwise a solution of 365 mg of succinyl chloride in 3 ml of acetonitrile. The mixture was allowed to stand 4 hours and then added with stirring to 125 ml of water. The mixture was stirred 15 minutes, then the solid was collected, dried, dissolved in 50 ml of chloroform and filtered through hydrous magnesium silicate, washing with 600 ml of chloroform. The filtrate was evaporated to a white glass. The addition of methanol and chilling gave crystals which were washed with cold methanol, then ether and dried, giving 785 mg of the desired intermediate as white crystals, m.p. 220° C.

EXAMPLE 5

(1,4-Dioxo-1,4-butanediyl)bis(imino-4,1-phenylene)-bis(1-thio-β-D-glucopyranosiduronic acid), dimethyl ester (1,4-Dioxo-1,4-butanediyl)bis(imino-4,1-phenylene)-bis(2,3,4-tri-O-acetyl-1-thio-β-D-glucopyranosiduronic acid), dimethyl ester may be converted to the desired intermediate essentially by the procedure of Example 2.

EXAMPLE 6

Hexasodium (1,4-dioxo-1,4-butanediyl)bis(imino-4,1-phenylene)-bis(2,3,4-tri-O-sulfo-1-thio-β-D-glucopyranosiduronic acid), dimethyl ester (1,4-Dioxo-1,4-butanediyl)bis(imino-4,1-phenylene)-bis(1-thio-β-D-glucopyranosiduronic acid), dimethyl ester may be converted to the desired product essentially by the procedure of Example 3.

EXAMPLE 7

(1,5-Dioxo-1,5-pentanediyl)bis(imino-4,1-phenylene)-bis(2,3,4-tri-O-acetyl-1-thio-β-D-glucopyranosiduronic acid), dimethyl ester To a solution of 2.0 g of 4-aminophenylthio 2,3,4-tri-O-acetyl-β-D-glucopyranosiduronic acid, methyl ester in 20 ml of pyridine:acetonitrile (1:1) under argon, with swirling, was added a solution of 383 mg of glutaryl chloride in 3 ml of acetonitrile. The procedure of Example 1 was followed, giving 1.8 g of the desired intermediate as a cream colored foam.

EXAMPLE 8

(1,5-Dioxo-1,5-pentanediyl)bis(imino-4,1-phenylene)-bis(1-thio-β-D-glucopyranosiduronic acid)

To a solution of 1.7 g of (1,5-dioxo-1,5-pentanediyl)-bis(imino-4,1-phenylene)bis(2,3,4-tri-O-acetyl-1-thio-β-D-glucopyranosiduronic acid), dimethyl ester in 30 ml of methanol was added 1.74 ml of 5 N sodium hydroxide with stirring, under an argon atmosphere. Stirring was continued for one hour, then 2.0 ml of 6 N glacial acetic acid was added and the solution was taken to dryness. The residue was evaporated three times from toluene, giving a glass which was triturated with 150 ml of absolute ethanol, giving 1.29 g of the desired intermediate as an amorphous solid.

EXAMPLE 9

Octasodium (1,5-dioxo-1,5-pentanediyl)bis(imino-4,1-phenylene)-bis(2,3,4-tri-O-sulfo-1-thio-β-D-glucopyranosiduronic acid)

A 5.18 g portion of triethylamine-sulfur trioxide complex was reacted with 1.0 g of (1,5-dioxo-1,5-pentanediyl)bis(imino-4,1-phenylene)bis(1-thio-β-D-glucopyranosiduronic acid) and then with sodium acetate as described in Example 3, giving 1.13 g of the desired product as a cream colored amorphous solid.

EXAMPLE 10

| Preparation of Compressed Tablet | |
|---|---|
| Ingredient | mg/Tablet |
| Active Compound | 0.5–500 |
| Dibasic Calcium Phosphate N F | qs |

-continued

| Preparation of Compressed Tablet | |
|---|---|
| Ingredient | mg/Tablet |
| Starch USP | 40 |
| Modified Starch | 10 |
| Magnesium Stearate USP | 1-5 |

EXAMPLE 11

| Preparation of Compressed Tablet - Sustained Action | |
|---|---|
| Ingredient | mg/Tablet |
| Active Compound as Aluminum Lake*, Micronized | 0.5-500 (as acid equivalent) |
| Dibasic Calcium Phosphate N F | qs |
| Alginic Acid | 20 |
| Starch USP | 35 |
| Magnesium Stearate USP | 1-10 |

*Complement inhibitor plus aluminum sulfate yields aluminum complement inhibitor. Complement inhibitor content in aluminum lake ranges from 5-30%.

EXAMPLE 12

| Preparation of Hard Shell Capsule | |
|---|---|
| Ingredient | mg/Capsule |
| Active Compound | 0.5-500 |
| Lactose, Spray Dried | qs |
| Magnesium Stearate | 1-10 |

EXAMPLE 13

| Preparation of Oral Liquid (Syrup) | |
|---|---|
| Ingredient | % W/V |
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 14

| Preparation of Oral Liquid (Elixir) | |
|---|---|
| Ingredient | % W/V |
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 15

| Preparation of Oral Suspension (Syrup) | |
|---|---|
| Ingredient | % W/V |
| Active Compound as Aluminum Lake, Micronized | 0.05-5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |

-continued

| Preparation of Oral Suspension (Syrup) | |
|---|---|
| Ingredient | % W/V |
| Purified Water qs ad | 100.0 |

EXAMPLE 16

| Preparation of Injectable Solution | |
|---|---|
| Ingredient | % W/V |
| Active Compound | 0.05-5 |
| Benzyl Alcohol N F | 0.9 |
| Water for Injection | 100.0 |

EXAMPLE 17

| Preparation of Injectable Oil | |
|---|---|
| Ingredient | % W/V |
| Active Compound | 0.05-5 |
| Benzyl Alcohol | 1.5 |
| Sesame Oil qs ad | 100.0 |

EXAMPLE 18

| Preparation of Intra-Articular Product | |
|---|---|
| Ingredient | Amount |
| Active Compound | 2-20 mg |
| NaCl (physiological saline) | 0.9% |
| Benzyl Alcohol | 0.9% |
| Sodium Carboxymethylcellulose | 1-5% |
| pH adjusted to 5.0-7.5 | |
| Water for Injection qs ad | 100% |

EXAMPLE 19

| Preparation of Injectable Depo Suspension | |
|---|---|
| Ingredient | % W/V |
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol N F | 0.9 |
| HCl to pH 6-8 | qs |
| Water for Injection qs ad | 100.0 |

EXAMPLE 20

| Preparation of Dental Paste | |
|---|---|
| Ingredient | % W/V |
| Active Compound | 0.05-5 |
| Zinc Oxide | 15 |
| Polyethylene Glycol 4000 USP | 50 |
| Distilled Water qs | 100 |

EXAMPLE 21

| Preparation of Dental Ointment | |
|---|---|
| Ingredient | % W/W |
| Active Compound | 0.05-5 |

-continued

| Preparation of Dental Ointment | |
|---|---|
| Ingredient | % W/W |
| Petrolatum, White USP qs | 100 |

EXAMPLE 22

| Preparation of Topical Ointment | |
|---|---|
| Ingredient | % W/W |
| Active Compound | 0.05–5 |
| Cholesterol | 3 |
| Stearyl Alcohol | 3 |
| White Wax | 8 |
| Petrolatum, White USP qs | 100 |

EXAMPLE 23

| Preparation of Spray Lotion (Non-aerosol) | |
|---|---|
| Ingredient | % W/W |
| Active Compound | 0.05–5 |
| Isopropyl Myristate | 20 |
| Alcohol (Denatured) qs | 100 |

EXAMPLE 24

| Preparation of Buccal Tablet | |
|---|---|
| Ingredient | g/Tablet |
| Active Ingredient | 0.00325 |
| 6 x Sugar | 0.29060 |
| Acacia | 0.01453 |
| Soluble Starch | 0.01453 |
| Soluble Starch | 0.01453 |
| F.D. & C. Yellow No. 6 Dye | 0.00049 |
| Magnesium Stearate | 0.00160 |
| | 0.32500 |

The final tablet will weigh about 325 mg and may be compressed into buccal tablets in flat faced or any other tooling shape convenient for buccal administration.

EXAMPLE 25

| Preparation of Dental Cream | |
|---|---|
| Ingredient | % W/W |
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 26

| Preparation of Topical Cream | |
|---|---|
| Ingredient | % W/W |
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |

-continued

| Preparation of Topical Cream | |
|---|---|
| Ingredient | % W/W |
| Propyl Paraben USP | 0.02 |
| Purified Water qs | 100 |

EXAMPLE 27

| Preparation of Lozenge | |
|---|---|
| Ingredient | g./Lozenge |
| Active Ingredient | 0.0140 |
| Kompact ® Sugar (Sucrest Co.) | 0.7138 |
| 6 x Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into ⅝" flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint/week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as nontoxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form," as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification of the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement modulating activity of compounds of this invention has been demonstrated by Test Code 026 (C1 inhibitor). This test measures the ability of activated human C1 to destroy fluid phase human C2 in the presence of C4 and appropriate dilutions of the test compound. An active inhibitor protects C2 from C1 and C4. The principal compound of the invention octasodium N,N′-bis[4-[(2,3,4,6-tetra-O-sulfo-β-D-glucopyranosyl)thio]phenyl]pentanediamide is active at a level of 7 wells in the Code 026 test.

We claim:

1. A compound selected from those of the formula:

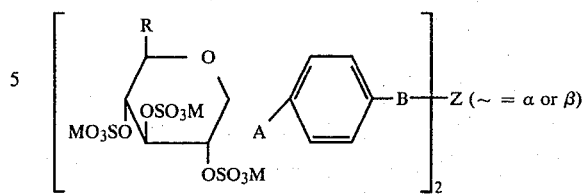

wherein M is a nontoxic pharmaceutically acceptable cation salt, wherein the salt forming moiety is selected from the group consisting of alkali metal, alkaline earth metal, aluminum, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$); A is selected from the group consisting of —S— and —O—; B is selected from the group consisting of —NHCO—, —NHSO$_2$— and —NHCH$_2$—; R is selected from the group consisting of CH$_2$OSO$_3$M, COOCH$_3$ and COOM; and Z is a straight or branched chain alkylidene group —(CH$_2$)$_m$—, where m is an integer 0–12, inclusive, with the proviso that when m is zero or one, B cannot be —NHSO$_2$—.

2. The compound according to claim 1, octasodium N,N′-bis[4-[(2,3,4,6-tetra-O-sulfo-β-D-glucopyranosyl)-thio]phenyl]pentanediamide, having the structure

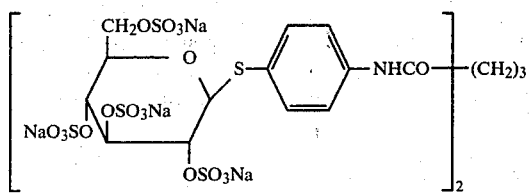

3. The compound according to claim 1, hexasodium (1,4-dioxo-1,4-butanediyl)bis(imino-4,1-phenylene)-bis(2,3,4-tri-O-sulfo-1-thio-β-D-glucopyranosiduronic acid), dimethyl ester, having the structure

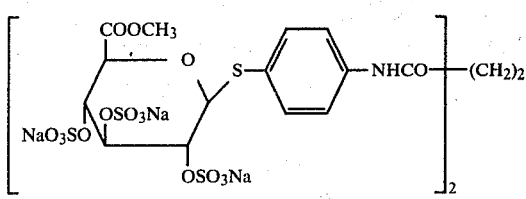

4. The compound according to claim 1, octasodium (1,5-dioxo-1,5-pentanediyl)bis(imino-4,1-phenylene)-bis(2,3,4-tri-O-sulfo-1-thio-β-D-glucopyranosiduronic acid), having the structure

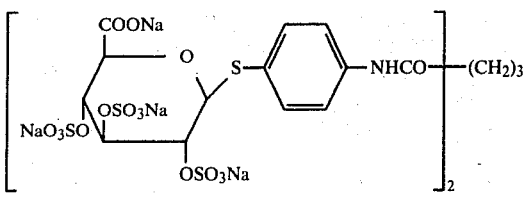

5. The compound according to claim 1, octatriethylammonium N,N′-bis[4-[(2,3,4,6-tetra-O-sulfo-β-D- glucopyranosyl)thio]phenyl]pentanediamide, having the structure

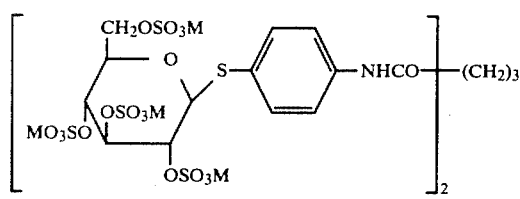

wherein M is NH⁺(C₂H₅)₃.

6. The compound according to claim 1, hexatriethylammonium (1,4-dioxo-1,4-butanediyl)bis(imino-4,1-phenylene)bis(2,3,4-tri-O-sulfo-1-thio-β-D-glucopyranosiduronic acid), dimethyl ester, having the structure

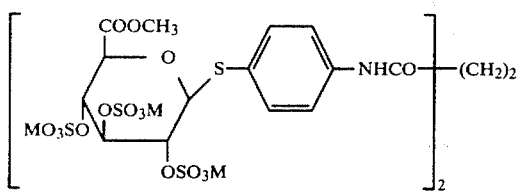

wherein M is NH⁺(C₂H₅)₃.

7. The compound according to claim 1, octatriethylammonium (1,5-dioxo-1,5-pentanediyl)bis(imino-4,1-phenylene)bis(2,3,4-tri-O-sulfo-1-thio-β-D-glucopyranosiduronic acid), having the structure

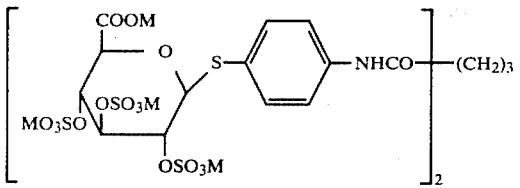

wherein M is NH⁺(C₂H₅)₃.

8. A compound selected from those of the formula:

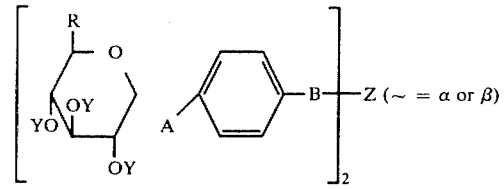

wherein Y is selected from the group consisting of —H and —COCH₃; A is selected from the group consisting of —S— and —O—; B is selected from the group consisting of —NHCO—, —NHSO₂— and —NHCH₂—; R is selected from the group consisting of —CH₂OY, —COOH and —COOCH₃; and Z is a straight or branched chain alkylidene group —(CH₂)ₘ—, where m is an integer 0–12, inclusive, with the proviso that when m is zero or one, B cannot be —NHSO₂—.

9. The compound according to claim 8, N,N'-bis[4-[(2,3,4,6-tetra-O-acetyl-β-D-glucopyranosyl)thio]-phenyl]pentanediamide, having the structure

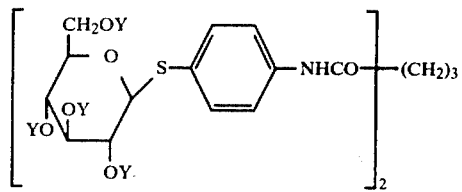

wherein Y is —COCH₃.

10. The compound according to claim 8, N,N'-bis[4-[(β-D-glucopyranosyl)thio]phenyl]pentanediamide, having the structure

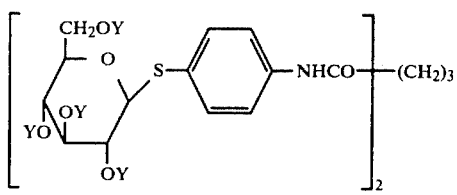

wherein Y is H.

11. The compound according to claim 8, (1,4-dioxo-1,4-butanediyl)bis(imino-4,1-phenylene)bis(2,3,4-tri-O-acetyl-1-thio-β-D-glucopyranosiduronic acid), dimethyl ester, having the structure

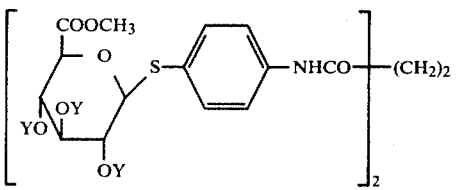

wherein Y is —COCH₃.

12. The compound according to claim 8, (1,4-dioxo-1,4-butanediyl)bis(imino-4,1-phenylene)bis(1-thio-β-D-glucopyranosiduronic acid), dimethyl ester, having the structure

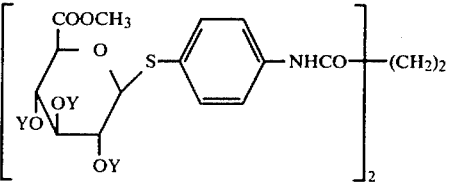

wherein Y is —COCH₃.

13. The compound according to claim 8, (1,5-dioxo-1,5-pentanediyl)bis(imino-4,1-phenylene)bis(2,3,4-tri-O-acetyl-1-thio-β-D-glucopyranosiduronic acid), dimethyl ester, having the structure

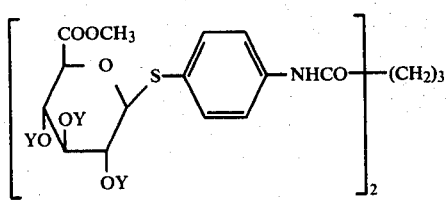

wherein Y is —COCH₃.

14. The compound according to claim 8, (1,5-dioxo-1,5-pentanediyl)bis(imino-4,1-phenylene)bis(1-thio-β-D-glucopyranosiduronic acid), having the structure

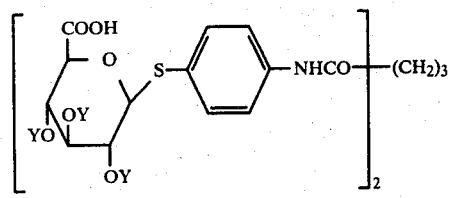

wherein Y is H.

15. A method of modulating the complement system in a body fluid which comprises subjecting said body fluid to the action of an effective complement modulating amount of a pharmaceutically acceptable compound selected from those of the formula of claim 1.

16. The method according to claim 15, wherein the body fluid is blood serum.

17. A method of modulating the complement system in a warm-blooded animal which comprises administering to said warm-blooded animal an effective complement modulating amount of a pharmaceutically acceptable compound selected from those of the formula of claim 1.

18. The method according to claim 15 or 17, wherein the compound is octasodium N,N'-bis[4-[(2,3,4,6-tetra-O-sulfo-β-D-glucopyranosyl)thio]phenyl]pentanediamide.

19. The method according to claim 15 or 17, wherein the compound is hexasodium (1,4-dioxo-1,4-butanediyl)bis(imino-4,1-phenylene)bis(2,3,4-tri-O-sulfo-1-thio-β-D-glucopyranosiduronic acid), dimethyl ester.

20. The method according to claim 15 or 17, wherein the compound is octasodium (1,5-dioxo-1,5-pentanediyl)bis(imino-4,1-phenylene)bis(2,3,4-tri-O-sulfo-1-thio-β-D-glucopyranosiduronic acid).

21. The method according to claim 15 or 17, wherein the compound is octatriethylammonium N,N'-bis[4-[(2,3,4,6-tetra-O-sulfo-β-D-glucopyranosyl)thio]phenyl]pentanediamide.

22. The method according to claim 15 or 17, wherein the compound is hexatriethylammonium(1,4-dioxo-1,4-butanediyl)bis(imino-4,1-phenylene)bis(2,3,4-tri-O-sulfo-1-thio-β-D-glucopyranosiduronic acid), dimethyl ester.

23. The method according to claim 15 or 17, wherein the compound is octatriethylammonium(1,5-dioxo-1,5-pentanediyl)bis(imino-4,1-phenylene)bis(2,3,4-tri-O-sulfo-1-thio-β-D-glucopyranosiduronic acid).

24. The method according to claim 17, wherein the compound is administered internally.

25. The method according to claim 17, wherein the compound is administered topically.

26. The method according to claim 17, wherein the compound is administered periodontally in the oral cavity.

27. The method according to claim 17, wherein the compound is administered intra-articularly.

28. The method according to claim 17, wherein the compound is administered parenterally.

29. A process for the preparation of a compound of the formula:

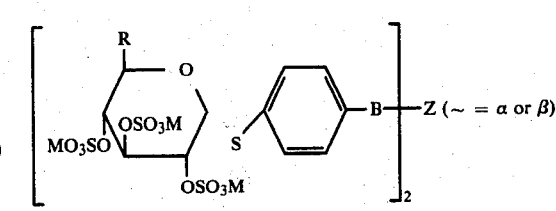

wherein M is a nontoxic pharmaceutically acceptable cation salt, wherein the salt forming moiety is selected from the group consisting of alkali metal, alkaline earth metal, aluminum, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$); B is selected from the group consisting of —NHCO—, —NHSO₂— and —NHCH₂—; R is selected from the group consisting of CH₂OSO₃M, COOCH₃ and COOM; and Z is a straight or branched chain alkylidene group —(CH₂)$_m$—, where m is an integer 0–12, inclusive, with the proviso that when m is zero or one, B cannot be —NHSO₂—, which comprises reacting a mixture of sodium hydride in oil dispersion in dimethoxyethane under an inert atmosphere with a solution of aminothiophenol in dimethoxyethane; stirring for 2 to 3.5 hours; adding a solution of a bromoacetyl pyranoside in dimethoxyethane; stirring overnight; reacting with an acid chloride of the formula:

where m is an integer 0–12, in acetonitrile under an inert atmosphere for 2 to 4 hours; reacting with ammonia-saturated methanol at −5° to +5° C. for 2 hours; reacting with triethylamine-sulfur trioxide in N,N-dimethylacetamide at 60°–65° C. under an inert atmosphere for 4 hours, giving the polytriethylammonium derivative of the above formula where M is NH⁺(C₂H₅)₃; reacting with a cation-containing compound wherein the salt forming moiety is selected from the group consisting of alkali metal, alkaline earth metal, aluminum, ammonia and substituted ammonia selected from the group consisting of piperidine, pyrazine, alkanolamine ($C_2$–$C_6$) and cycloalkylamine ($C_3$–$C_6$), and precipitating in ethanol, giving the final product.

* * * * *